(12) United States Patent
Dong et al.

(10) Patent No.: US 11,674,707 B2
(45) Date of Patent: Jun. 13, 2023

(54) SYSTEM FOR MINIMIZING INDOOR INFECTION RISK AND MAXIMIZING ENERGY SAVINGS

(71) Applicants: Bing Dong, Manlius, NY (US); Jianshun Zhang, Jamesville, NY (US)

(72) Inventors: Bing Dong, Manlius, NY (US); Jianshun Zhang, Jamesville, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 0 days.

(21) Appl. No.: 17/544,383

(22) Filed: Dec. 7, 2021

(65) Prior Publication Data
US 2022/0178574 A1 Jun. 9, 2022

Related U.S. Application Data

(60) Provisional application No. 63/122,460, filed on Dec. 7, 2020.

(51) Int. Cl.
| | |
|---|---|
| *F24F 8/10* | (2021.01) |
| *F24F 11/65* | (2018.01) |
| *F24F 11/46* | (2018.01) |
| *F24F 11/74* | (2018.01) |
| *F24F 11/80* | (2018.01) |
| *F24F 11/58* | (2018.01) |

(Continued)

(52) U.S. Cl.
CPC .............. *F24F 11/65* (2018.01); *F24F 11/46* (2018.01); *F24F 11/58* (2018.01); *F24F 11/74* (2018.01); *F24F 11/80* (2018.01); *G05B 19/042* (2013.01); *G16H 50/30* (2018.01); *F24F 8/10* (2021.01); *F24F 2011/0002* (2013.01); *F24F 2120/10* (2018.01); *F24F 2130/10* (2018.01); *F24F 2140/40* (2018.01); *G05B 2219/2614* (2013.01)

(58) Field of Classification Search
CPC .. F24F 11/65; F24F 11/46; F24F 11/58; F24F 11/74; F24F 11/80; F24F 8/10; F24F 2011/0002; F24F 2120/10; F24F 2130/10; F24F 2140/40; F24F 11/62; F24F 2110/10; F24F 2110/50; G05B 19/042; G05B 2219/2614; G05B 15/02; G16H 50/30; G16H 40/63; G16H 40/67; Y02B 30/70
See application file for complete search history.

(56) References Cited

U.S. PATENT DOCUMENTS

| | | | | |
|---|---|---|---|---|
| 2014/0041401 | A1* | 2/2014 | Douglas | F25B 43/00 62/89 |
| 2019/0366793 | A1* | 12/2019 | Giordano | B60H 1/00742 |

(Continued)

*Primary Examiner* — Michael W Choi
(74) *Attorney, Agent, or Firm* — David Nocilly

(57) ABSTRACT

A system and method for minimizing indoor infection risk and improving indoor air quality (IAQ) while maximizing energy savings. The system integrates occupancy detection and forecasting, outdoor weather conditions and forecasting, indoor infection risks and air quality modeling, any tunable air filtration, the clean air delivery rate, and any portable air cleaners. The system outputs the total amount of outdoor air intake, the air temperature of the supply air into the space, the supply air flow rate into the space, the operation mode of tunable air filtration/purification/disinfection, the operation mode of the in-room air cleaner, and space/room temperature set-points, and thus can serve as the central controller for an HVAC system.

20 Claims, 5 Drawing Sheets

(51) Int. Cl.
  *G16H 50/30* (2018.01)
  *G05B 19/042* (2006.01)
  *F24F 130/10* (2018.01)
  *F24F 11/00* (2018.01)
  *F24F 120/10* (2018.01)
  *F24F 140/40* (2018.01)

(56) References Cited

U.S. PATENT DOCUMENTS

| | | | |
|---|---|---|---|
| 2020/0240668 A1* | 7/2020 | Bassa | G05B 15/02 |
| 2021/0011444 A1* | 1/2021 | Risbeck | F24F 8/20 |
| 2021/0080915 A1* | 3/2021 | Yan | F24F 11/46 |
| 2022/0010996 A1* | 1/2022 | Carrieri | F24F 11/63 |
| 2022/0042694 A1* | 2/2022 | He | F24F 11/88 |

* cited by examiner

SYSTEM FOR MINIMIZING INDOOR INFECTION RISK AND MAXIMIZING ENERGY SAVINGS

BACKGROUND OF THE INVENTION

1. Field of the Invention

The present invention relates to heating, ventilation, and air conditioning (HVAC) systems and, more specifically, to an approach for controlling an HVAC system to minimize indoor infection risk and the concentrations of air contaminants of interest while maximizing energy savings through optimal ventilation, tunable air cleaning and temperature control and their integration.

2. Description of the Related Art

An indoor environment is traditionally maintained by the heating, ventilation, and air conditioning (HVAC) system of using appropriate temperature and ventilation controls. Conventional control approaches focus on how to improve indoor environment through ventilation controls or save energy through model predictive controls. These control approaches do not, however, take into account the need to minimize infection risk indoors and in order to reduce infection risk most buildings will simply increase outdoor air intake and/or install higher performance air filters, both of which increases the energy consumption of HVAC system. Accordingly, there is a need for an HVAC control system that can minimize indoor infection risk and the concentrations of air contaminants of interest while maximizing energy savings through optimal ventilation, tunable air cleaning and temperature control.

BRIEF SUMMARY OF THE INVENTION

The present invention is a system and method for minimizing indoor infection risk and improving indoor air quality by reducing concentrations of pollutants of interest while maximizing energy savings that integrates real-time occupancy detection and forecasting that determines the current and future occupancy in a space (presence and people counting), outdoor weather condition forecasting that provides current and future outdoor weather information, indoor infection risk and air quality models that model the infection risk assuming an imperfectly mixed realistic indoor air environment as well as the concentrations of pollutants of interest for indoor air quality (IAQ) control, tunable air filtration/purification/disinfection technologies with different efficiency that provides different filtration/purification/disinfection efficiency and clean air delivery rate in the HVAC system for removing and diluting the virus-containing particles, and any portable air purifier/cleaner devices that provide the infectious particle removal rate (or fresh air supply rate) by air cleaners. The present invention outputs the total amount of outdoor air intake, the air temperature of the supply air into the space, the supply air flow rate into the space, the operation mode of tunable air filtration/purification/disinfection, the operation mode of the in-room air cleaner, and space/room temperature set-points, and thus can serve as the central controller for an entire HVAC system. The present invention can thus transform existing model predictive control capability to meet indoor infection risk control and indoor air quality (IAQ) requirements while maximize the energy savings.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
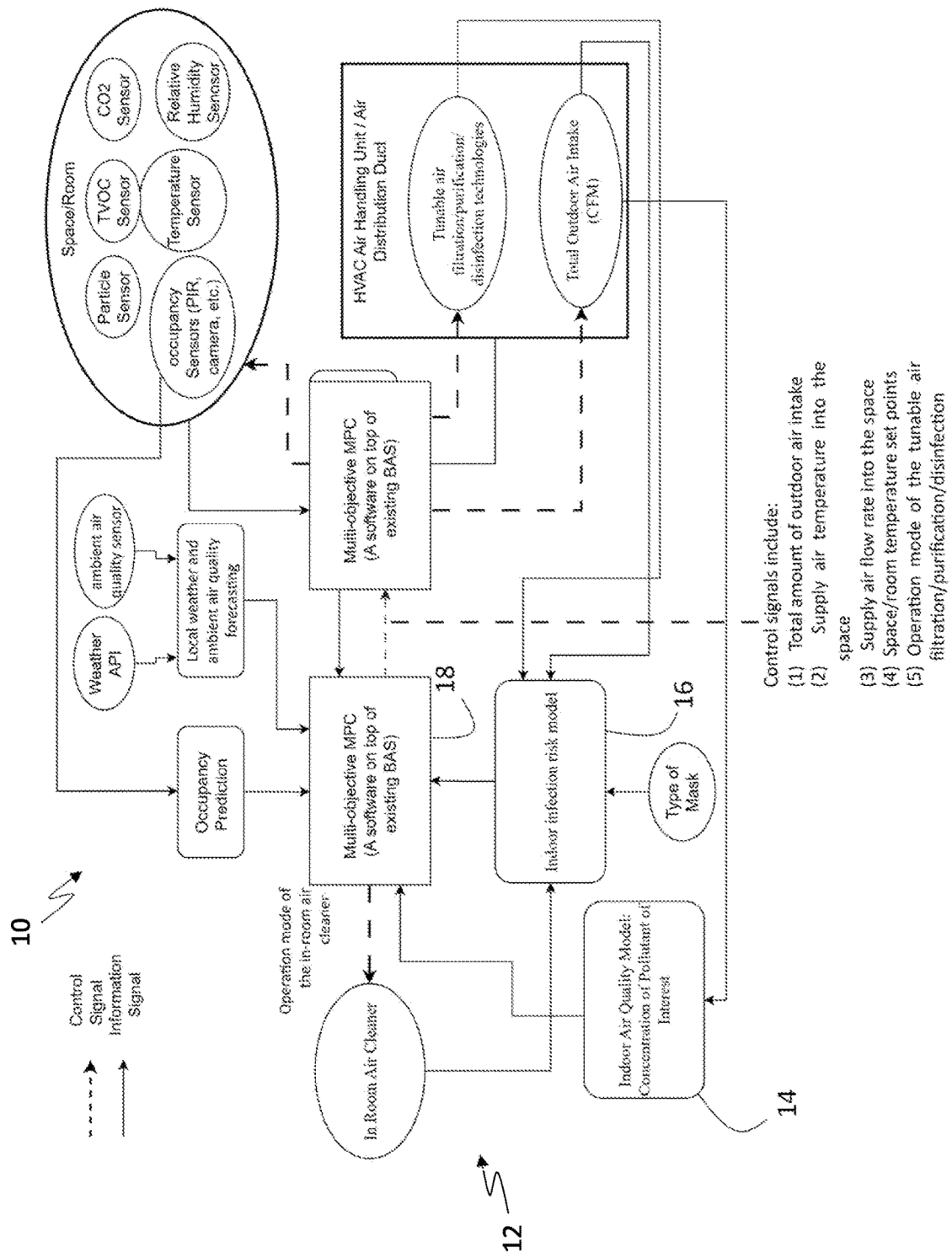
FIG. 1 is a schematic of overview HVAC control system according to the present invention.

Referring to the figures, wherein like numeral refer to like parts throughout, there is seen in FIG. 1 a schematic of a building HVAC system 10 including a control system 12 according to the present invention. System 12 includes three primary components, an indoor air quality model 14, an indoor infection risk model 16, and a multi-objective MPC 18. Multi-objective MPC receives data from all of the components of the HVAC system 10, calculates the appropriate control settings to implement a control strategy that minimizes indoor infection risk while maximizing energy savings through optimal ventilation, tunable air cleaning and temperature control, and outputs the appropriate control signal to the components of the HVAC system 10 to implement the determined control strategy.

Control system 12 is based on a predictive control strategy to integrate occupancy prediction, weather forecasting, indoor infection risk modeling and building automation system. The disclosed overall architecture leverages building automation system information through BACnet™, and develops MPC platform to minimize indoor infection risk while maximizing energy savings. The system architecture is designed to compute and implement the optimized control strategy by forecasting future states of occupancy (presence and number of occupants), forecasting future states of local weather (temperature and solar radiation), forecasting future states of ambient air quality, forecasting future room heating and cooling loads, forecasting future states of room temperature and indoor air quality, communicating with building automation system to obtain current and historical room temperature and indoor air quality, and communicating with building automation system to obtain current operation mode of tunable air filtration/purification/disinfection. All computations may be performed by cloud computing or by local computers or controllers or any types of processors. System implement may be performed Internet of Things (IOTs) enabled components. Control system 12 is designed to fulfill the following functions: optimize total amount of outdoor air intake amount and its schedule; optimize supply air temperature into the space and its schedule; optimize supply air flow rate into the space and its schedule; optimize room/space temperature setpoint and its schedule; optimize operation mode of the tunable air filtration/purification/disinfection and its schedule; and optimize operation mode of the in-room air cleaner on/off and its schedule.

Control system 12 includes a multi-objective model predictive control design, energy and IAQ management and optimization using modeling components in overall model predictive control design. The overall model predictive control modeling components include an occupancy prediction model, a local weather (temperature and solar radiation forecasting) model, a local ambient air quality forecasting model, a room/space heating and cooling load forecasting model, an indoor infection risk model, an indoor air quality model, a building physics-based model, and an HVAC physics-based model. These components are seen in FIG. 1.

Referring to FIG. 1, hardware devices are depicted in oval shapes and include: in-room occupancy sensors; HVAC system including air handing units (AHU), fans, pumps, and terminal units for large commercial buildings, in-room sensors for temperature, relative humidity, particle sensors, TVOC, $CO_2$; tunable air filtration/purification/disinfection technologies in AHU, in-room air cleaner; ambient air quality sensor; and the type of mask worn by a human occupant (if any).

The integrated control, energy and IAQ management, and optimization system makes decisions based on: infection risk and IAQ models that predict the infection risk and the concentration of the indoor air contaminants of interest based on outdoor air intake flow rate and air quality, total supply airflow rate, operation mode and efficiency of the tunable air filtration/purification/disinfection technologies, in room air cleaner and type of mask; room/space load forecasting; occupants' thermal comfort preferences; occupants' schedule forecasting; room/space control state estimation; room/space air quality states; room/space operational constraints; and weather forecasting. The integrated control, energy and IAQ management, and optimization system communicates these decisions and constraints by dispatching heating, cooling and ventilation set-points (e.g., thermostat set-points, air handling unit airflow rate, and supply air temperature set-points) to the local device controllers. The system has decision-making capabilities to control heating, cooling and ventilation system over a time horizon.

The system has an optimization engine that computes schedules of outdoor air intake airflow rate, supply air temperature, supply airflow rate, room set points for temperature, RH and target pollutant concentrations, operation mode of the tunable air filtration and operation mode of the in-room air cleaner based on the information it collects. The main features of the optimization engine include: a multi-objective model predictive control architecture, and a mixed integer programming formulation to solve both continuous and discrete equipment controls such as in-room air cleaners. The disclosed system has three different approaches to solve the MPC problem and implement control outputs in real-time. The user can choose any of those three approaches based on the availability of onsite computing resources.

Figure 2:
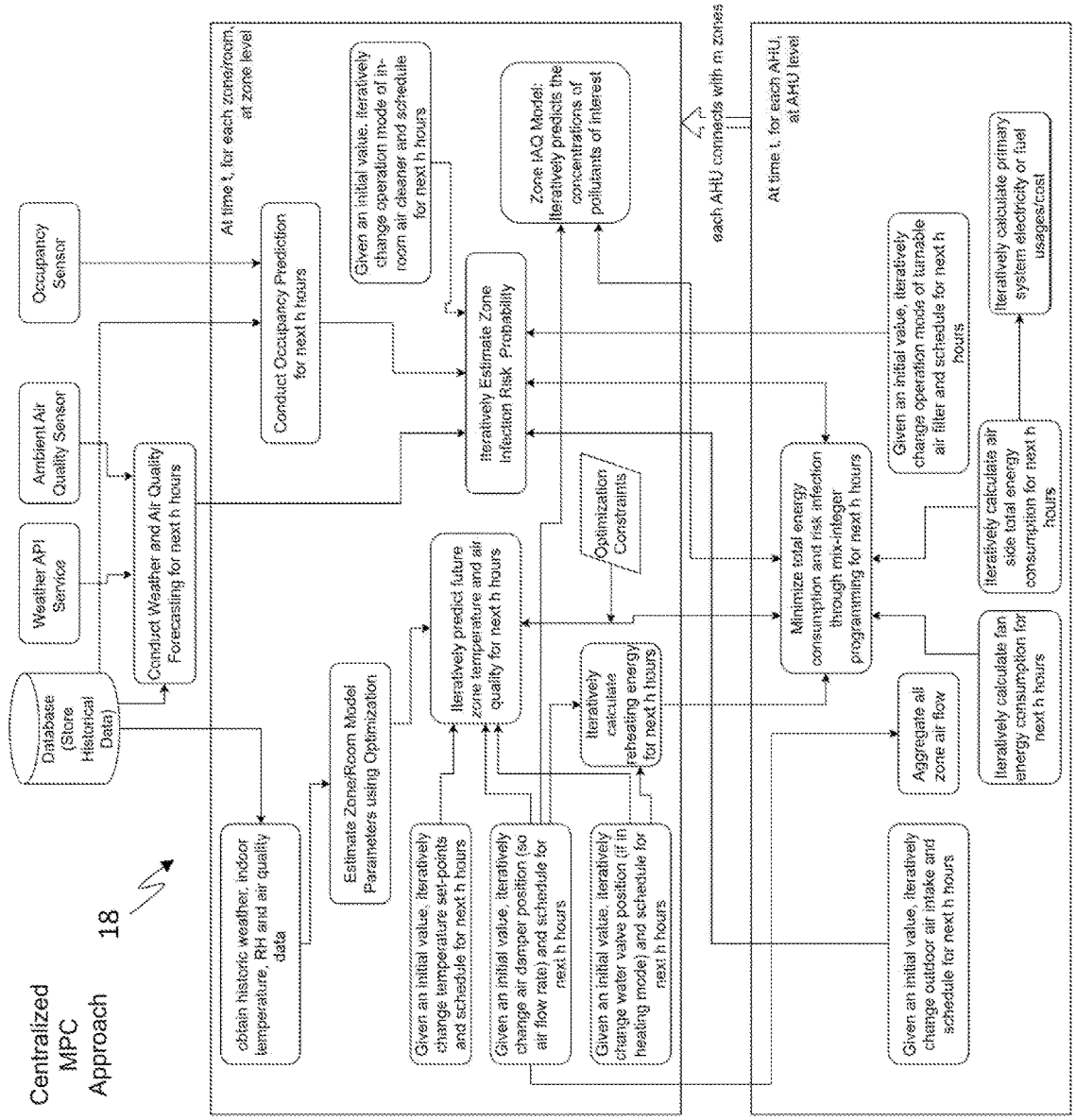
FIG. 2 is a schematic of a centralized MPC approach according to the present invention.

First, is an online centralized MPC at each AHU level as shown in FIG. 2. In this approach, the optimization is solved at a supervisory level, and implemented at each AHU level.

Figure 3:
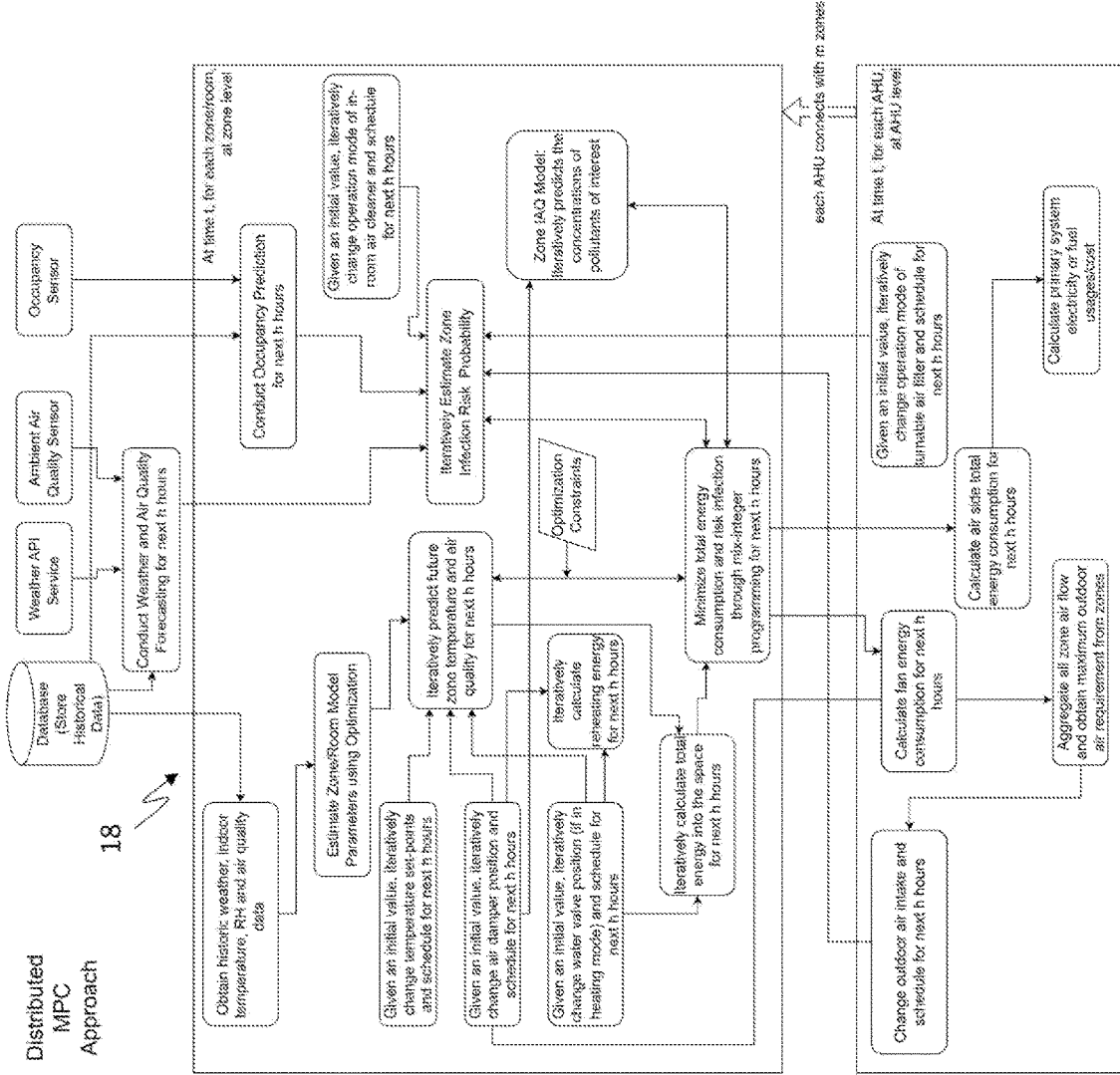
FIG. 3 is a schematic of a distributed MPC approach according to the present invention.

Second, an online distributed MPC at zone level as shown in FIG. 3. In this approach, the optimization is solved at each room/zone level and implemented at room/zone level.

Figure 4:
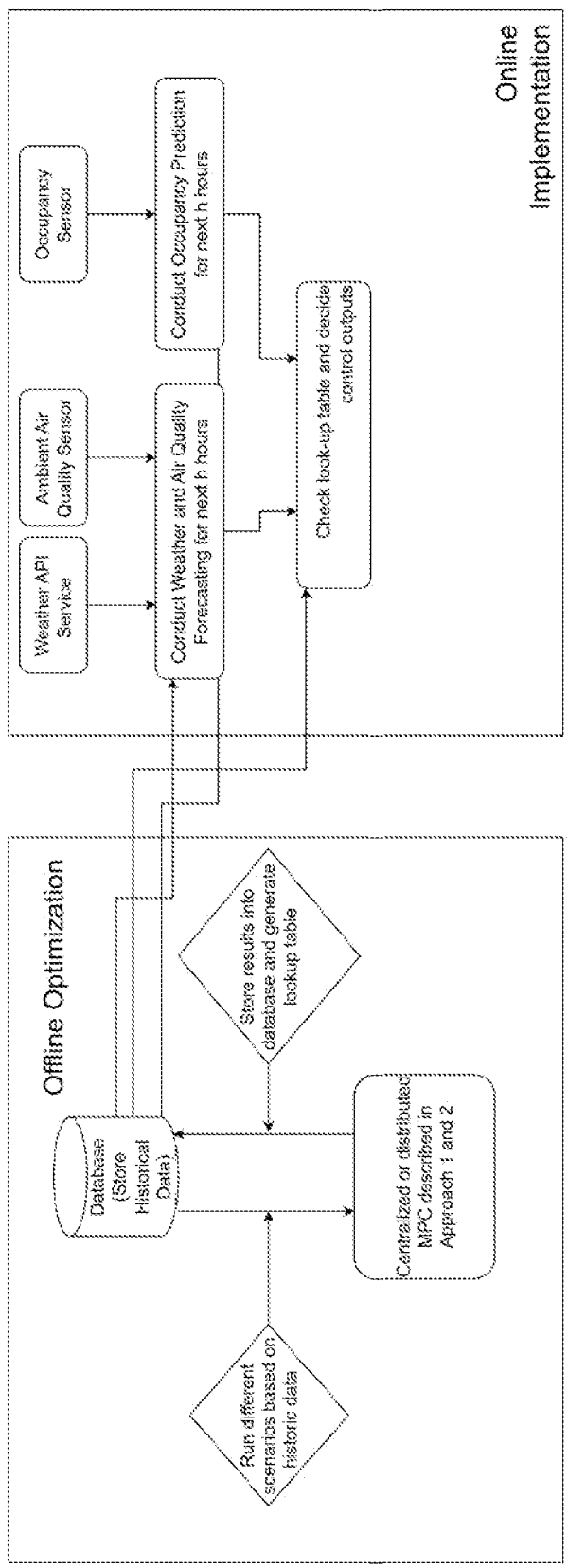
FIG. 4 is a high-level schematic of an offline learned MPC approach according to the present invention.

Third, offline learning as shown in FIG. 4. In this approach, the system learns a large possible control outputs either using approaching 1 or approach 2 based on historic data. Such learning can be conducted every a few weeks. During the online implementation, the algorithms will look up in the database for similar boundary conditions (e.g. weather, air quality, number of people) and find corresponding control outputs.

Figure 5:
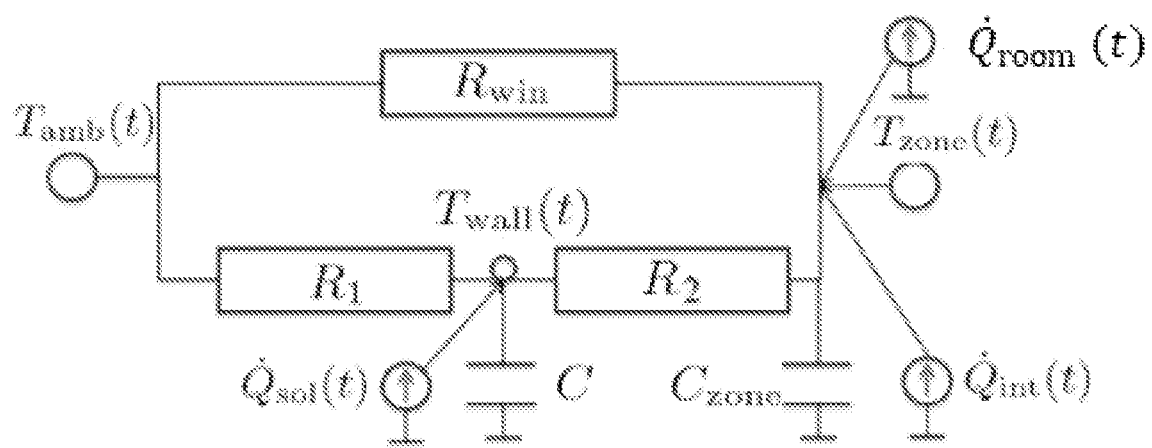
FIG. 5 is a schematic of a room/space thermal model according to the present invention.

Component Level Modeling according to the present invention includes a Room/Space Thermal Model, where A room$^l$ can be represented using a 3R2C model, as seen in FIG. 5

From the 3R2C model, the thermal dynamics of the room can be represented as follows:

$$\dot{T}_{wall} = \frac{T_{amb} - T_{wall}}{CR_2} + \frac{T_{zone} - T_{wall}}{CR_1} + \frac{\dot{Q}_{sol}}{C} \tag{1a}$$

$$\dot{T}_{zone} = \frac{T_{wall} - T_{zone}}{C_{zone}R_1} + \frac{T_{amb} - T_{zone}}{C_{zone}R_{win}} + \frac{\dot{Q}_{int} + \dot{Q}_{room}}{C_{zone}} \tag{1b}$$

Where $\dot{Q}_{room}$ is the total cooling or heating load injected into the room by the HVAC system, calculated as:

$$\dot{Q}_{room} = c \cdot \dot{m}_{room}(T_{supply,room} - T_{set}) \tag{2}$$

Further, the mass flow rate and air supply temperature to the room are functions of the damper position $\delta_{damp}$, and reheating coil valve position $\delta_{vav\_rh}$;

$$\dot{m}_{room} = f_{damp}(\delta_{damp}) \tag{3}$$

$$T_{supply,room} = f_T(\delta_{vav\_rh}, \delta_{damp}) \tag{4}$$

Substituting (3), (4) into (2) results in the room cooling or heating load being expressed in terms of three control variables $\delta_{vav\_rh}, \delta_{damp}, T_{set}$;

$$\dot{Q}_{room} = f_Q(\delta_{vav\_rh}, \delta_{damp}, T_{set}) = c \cdot f_{damp}(\delta_{damp}) \cdot (f_T(\delta_{vav\_rh}, \delta_{damp}) - T_{set}) \tag{5}$$

Thus, the dynamics of the room (1) can be expressed in a semi-linear form:

$$\dot{T}_{wall} = \frac{T_{amb} - T_{wall}}{CR_2} + \frac{T_{zone} - T_{wall}}{CR_1} + \frac{\dot{Q}_{sol}}{C} \tag{6a}$$

$$\dot{T}_{zone} = \frac{T_{wall} - T_{zone}}{C_{zone}R_1} + \frac{T_{amb} - T_{zone}}{C_{zone}R_{win}} + \frac{\dot{Q}_{int} + f_Q(\delta_{vav\_rh}, \delta_{damp}, T_{set})}{C_{zone}} \tag{6b}$$

These room dynamics can be written in state space form as follows:

$$\dot{x}_l^t = A_l x_l^t = B_l f(u_l^t) = E_l w_l^t \forall l \in \mathcal{L}, \forall t \in \mathcal{T} \tag{7}$$

where $x_l^t = [T_{wall}^t \ T_{zone}^t]_l^T$ is the state of the room (i.e., wall and zone temperatures);
$f(u_l^t) = f_Q(\delta_{vav\_rh}, \delta_{damp}, T_{set})_l^t$ is a nonlinear function of the three room-specific control input variables (VAV reheating coil position, damper position, setpoint temperature);
$w_l^t = [T_{amb}^t \ \dot{Q}_{sol}^t \ \dot{Q}_{int}^t]_l^T$ is the uncontrollable input at time t, comprised of ambient temperature, heat gains due to solar radiation, and internal heat gains due to occupants, lights, and equipment; and the system matrices $A_l$, $B_l$, $E_l$ are as follows:

$$A_l = \begin{bmatrix} -\frac{1}{C}\left(\frac{1}{R_1} + \frac{1}{R_2}\right) & \frac{1}{CR_1} \\ \frac{1}{C_{zone}R_1} & -\frac{1}{C_{zone}}\left(\frac{1}{R_1} + \frac{1}{R_{win}}\right) \end{bmatrix}_l \tag{8}$$

$$B_l = \begin{bmatrix} 0 \\ \frac{\mu}{C_{zone}} \end{bmatrix}_l$$

$$E_l = \begin{bmatrix} \frac{1}{CR_2} & \frac{1}{C} & 0 \\ \frac{1}{C_{zone}R_{win}} & 0 & \frac{1}{C_{zone}} \end{bmatrix} l$$

where $R_1$, $R_2$, $R_{win}$, $C$, $C_{zone}$ are the building thermal resistance and capacitance values and $\mu$ is the coefficient of performance of the AHU.

The HVAC model is based on the AHU which serves the entire building provides a total cooling or heating load according to its mass flow rate and temperature differential:

$$\dot{Q}_{AHU} = c \cdot \dot{m}_{AHU}(T_{supply,AHU} - T_{mix}) \quad (9)$$

The mass flow rate is a mixture of outdoor air intake and return air, with a being the fraction made up by outdoor air or outdoor air intake percentage:

$$\dot{m}_{AHU} = \alpha \cdot \dot{m}_{out} + (1-\alpha) \cdot \dot{m}_{return} \quad (10)$$

Therefore by substituting (10) into (9), the air side total cooling or heating load can be expressed in terms of AHU-specific control variables $u_{AHU} = [T_{supply,AHU}, \dot{m}A_{HU}, \alpha]$:

$$\dot{Q}_{AHU} = f_{AHU}(T_{supply,AHU}, \alpha) = c \cdot (\alpha \cdot \dot{m}_{out} + (1-\alpha) \cdot \dot{m}_{return}) \cdot (T_{supply,AHU} - T_{mix}) \quad (11)$$

The AHU model and room models are coupled through a mass flow balance (i.e., the total AHU flow rate is the sum of all n room flow rates):

$$\dot{m}_{AHU} = \dot{m}_1 + \dot{m}_2 + \ldots + \dot{m}_i + \ldots + \dot{m}_n \quad (12)$$

Finally, the total HVAC fan power use is calculated as a function of the total flow rate:

$$p_{fan} = f_{fan}(\dot{m}_{AHU}) \quad (13)$$

The Infection Risk Model is used to determine infection risk, which can be quantified by the well-known Wells-Riley equation [2]:

$$P = \frac{N_C}{N_S} = 1 - e^{-\frac{Iqpt}{V\Lambda}} \quad (14)$$

where $N_C$=the number of new cases in the space; $N_S$=the number of susceptible people; I=the number of virus carrier at the start of the exposure period; q=the infectious quantum generation rate per virus carrier (quanta/h per person); p=pulmonary ventilation rate (m³/h); t=exposure time (h); V=space air volume (m³); $\Lambda$=the fresh air change rate in the room (l/h).

Equation (5) establishes the relationship between the probability of infection (i.e., infection risk) in a perfectly mixed air space and the average viral dose exposure as:

$$P = 1 - e^{-D} \quad (15)$$

Where D=viral dose exposure (quanta). Note that 1 quantum is the amount of viral dose exposure needed to result in a probability of infection of 63% per Equation (5). The dose exposure for an individual in the space is calculated as follows:

$$D = -R_S R_I \frac{Iqpt}{V\Lambda} \quad (16)$$

Where $R_S$ and $R_I$=fraction of infectious particles passing through the mask worn by the virus carriers and the susceptibles, respectively; and $\Lambda$=the "total equivalent" clean air change rate for the space in terms of infection virus dilution due to the air cleaning devices in central HVAC system and/or within the room space as well as that from the outdoor air intake flow rate (outdoor ventilation rate). Equations (6) and (7) are used to predict the risk of infection for an individual in an indoor space accounting for the effects of ventilation, HVAC system supply and/or recirculated air cleaning, in-room air cleaners, and mask wearing [3].

The fraction of infectious particle penetrated through the mask or respirator for susceptible ($R_S$) and infected ($R_I$) population can be calculated by Eqn. 8 and 9, respectively. And both depend on the mask filtration efficiency ($\eta_S$ or $\eta_I$). The penetration fraction (R) equals 1 when no mask or respirator is used during the exposure period. An additional fractional factor ($f_R$) is multiplied by the original filtration efficiency of the mask to represent the fraction of time using a mask/respirator over the entire exposure period. It equals 1 when the mask is worn during the entire exposure period.

$$R_S = 1 - f_{R,S}\eta_S \quad (17)$$

$$R_I = 1 - f_{R,I}\eta_I \quad (18)$$

The "total effective" air change rate depends on the "effective" air change rates due to ventilation rate ($\lambda_{vent}$), pathogen inactivation rate ($k_{UV}$) by ultraviolet germicidal irradiation (UVGI) systems, infectious particle deposition rate ($k_{deposition}$) and pathogen natural inactivation rate in the air ($k_{inactivation}$), as shown in Eqn. 10. The "effective" air change rate includes the air change rate due to fresh air supply rate by the HVAC system ($\lambda_{HVAC}$ or $\dot{m}_{AHU}$), natural ventilation rate ($\lambda N_V$) and infectious particle removal rate by air purifiers ($k_{purifier}$). The fraction (f) of operation time over the entire exposure period is applied to each term in Eqn. 11 to determine the net overall ventilation rate. The fresh/clean air change rate supplied by the HVAC system ($\lambda_{HVAC}$ or $\dot{m}_{AHU}$) includes the outdoor part and the recirculated part. The recirculated fresh/clean air change rate (Eqn. 12) depends on the recirculated air change rate ($\lambda_{recirculated}$) and the filtration efficiency of the filters in the HVAC system for the virus-containing particles ($\eta_{filter}$). The natural ventilation air change rate ($\lambda_{NV}$) results from the airflows through openings and cracks on the building envelope.

$$\Lambda = \lambda_{vent} + f_{UV}k_{UV} + k_{deposition} + k_{inactivation} \quad (19)$$

$$\lambda_{vent} = f_{HVAC}k_{HVAC} + f_{NV}\lambda_{NV} + f_{purifier}k_{purifier} \quad (20)$$

$$\lambda_{HVAC} = \lambda_{outdoor} + \lambda_{recirculated}\eta_{filter} \quad (21)$$

An in-room air purifier can supply additional fresh/clean air to the space. The infectious particle removal rate (or fresh air supply rate) by air purifiers ($k_{purifier}$) can be estimated by its airflow rate ($\lambda_{purifier}$) and filter efficiency ($\eta_{purifier}$), or based on its clean air delivery rate (CADR) and room volume (V):

$$k_{purifier} = \lambda_{purifier}\eta_{purifier} = \frac{CADR}{V} \quad (22)$$

The actual ventilation rate ($\lambda_{vent}$) is a spatial-variable that depends on the particular location in the space. Thus, an additional factor is applied to the original equation in Eqn. 11 to adapt it to imperfect mixing scenarios. The infectious particle removal rates due to UVGI systems, deposition, and natural inactivation are assumed to be uniform in the whole space. Therefore, these terms do not have to be modified for imperfect mixing.

The pathogen removal rate by the UVGI system depends on the fraction of UVGI operation time ($f_{UV}$) and the pathogen inactivation rate due to UV irradiation ($k_{UV}$). The infectious particle deposition rate ($k_{deposition}$) relies on an approximate estimate of gravitational settling (Eqn. 14) from Nicas et al. [4], which depends on the particle diameter ($d_p$) and room height (H). It is assumed that the deposited particles will not be resuspended into the air space again.

$$k_{deposition} = \frac{0.108 \, d_p^2 \left(1 + \frac{0.166}{d_p}\right)}{H} \quad (23)$$

The pathogen natural inactivation rate is not considered, in part because of the lack of existing data on the size-resolved natural inactivation rate of SARS-CoV-2 and in part because quanta generation rates (q), when back-calculated using Eqn. 1, will inherently account for any inactivation that occurred during the case study period [5].

The IAQ model predicts the concentrations of pollutants of interest in the occupied zone and estimate the health risks associated with the occupant exposure to the various pollutants. The concentration of an individual pollutant (i) of interest is governed by the following zone mass balance equation:

$$V\frac{dC}{dt} = A_e E(t) + Q(C - C_s) + A_s S(t) \quad (24)$$

Where V=zone volume (m$^3$); C=concentration (ug/m$^3$); $A_e$=emission surface area (m$^2$); E(t) emission factor (i.e., emission rate per unit surface area, ug/h/m$^2$); Q=supply air volumetric flow rate to the zone (m$^3$/h) which is $$\frac{\dot{m}_{room}}{\rho};$$

$C_s$=concentration of the supply air which include the effects of ventilation and air cleaning in the central HVAC system (ug/m$^3$); $A_s$=Area of sink surfaces (m$^2$); S(t) sorption/filtration/cleaning rate by sinks including in-room air cleaners (ug/h/m$^2$).

The model is further extended to multizone buildings to account for the inter-zone pollutant transport [6]. The model is used to predict the concentrations over a time of horizon in the MPC model, and the predicted concentrations are compared to pre-established threshold limits for each pollutant of interest such as formaldehyde, PM2.5, CO$_2$, etc. for maintaining satisfactory IAQ in the buildings, or for estimating the health risk associated with the cumulative exposure to the pollutants.

The multi-objective model predictive control can implement a centralized MPC approach where a joint optimization objective can be designed to minimize the weighted sum of total AHU fan energy, total air side heating/cooling energy in an AHU, total zone reheating energy (if applicable), zone infection risk, and the concentrations of pollutants of interest (if applicable) for a prediction horizon h:

$$J^t = \rho_f p_{fan}^t + \rho_{coil} p_{AHU}^t + \rho_{rhz} p_{rhz}^t + \rho_{risk} p_{risk}^t + \rho_c p_c^t \quad (25)$$

Each term is weighted by a cost scalar $\rho(\cdot)$, and the overall objective is a time average of the sum of the five weighted terms. These weights and those in subsequent objective functions are tuned to achieve optimal control performance based on training data. Once tuned, the weights may remain static unless the underlying system models (i.e., room or AHU models) are changed. In addition, any cost function from utility companies could be added into all energy terms in Eq. (25). Thus, a centralized MPC controller will solve the following multi-objective problem for all room at an AHU level, over some prediction horizon h:

$$\text{minimize} \sum_{t=1}^{h} j^t(u_{AHU\_central}^t, u_{l\_central}^t) \quad (26)$$

subject to (7), (11), (12), (13), (14), (24)

$u_{AHU}^{min} \leq u_{AHU}^t \leq u_{AHU}^{max} \; \forall \, t = 1, \ldots, h$ $u_l^{min} \leq u_l^t \leq u_l^{max} \; \forall \, l = 1, \ldots, n, \; \forall \, t = 1, \ldots, h$ $x_l^{min} \leq x_l^t \leq x_l^{max} \; \forall \, l = 1, \ldots, n, \; \forall \, t = 1, \ldots, h$ where $u_{AHU\_central}^t = [T_{supply,AHU}^t, \dot{m}_{AHU}^t, \alpha^t, \eta_{filter}^t]$ are new control variables at the AHU level, and where $u_{l\_central}^t = [\delta_{vav_{rh},l}^t, \delta_{damp,l}^t, T_{set,l}^t, \eta_{purifier,l}^t, R_{s,l}, R_{l,l}]$ are new control variables at each room l.

In the distributed MPC approach, a joint optimization objective can be designed to minimize the weighted sum of total air side heating/cooling energy in each room, total zone reheating energy (if applicable), zone infection risk, and the concentrations of pollutants of interest (if applicable) for a prediction horizon h, for each room l:

$$J_l^t = \rho_{room} p_{room}^t + \rho_{rhz} p_{rhz}^t + \rho_{risk} p_{risk}^t + \rho_c p_c^t \quad (27)$$

Each term is weighted by a cost scalar and the overall objective is a time average of the sum of the four weighted terms. Thus, for each room, a MPC controller will solve the following multi-objective problem over some prediction horizon h:

$$\text{minimize} \sum_{t=1}^{h} j^t(u_{l\_dist}^t) \quad (28)$$

subject to (7), (11), (14), (24)

$u_l^{min} \leq u_l^t \leq u_l^{max} \; \forall \, l = 1, \ldots, n, \; \forall \, t = 1, \ldots, h$ $x_l^{min} \leq x_l^t \leq x_l^{max} \; \forall \, l = 1, \ldots, n, \; \forall \, t = 1, \ldots, h$ where $u_{l\_dist}^t = [\lambda_{outdoor,l}^t, \delta_{vav_{rh},l}^t, \delta_{damp,l}^t, T_{set,l}^t, \eta_{purifier,l}^t, R_{s,l}, R_{l,l}]$ are new control variables at each room l. $\lambda_{outdoor,l}^t$ is the required outdoor air portion of the total fresh air into each zone/room l.

As described above, the present invention may be a system, a method, and/or a computer program associated therewith and is described herein with reference to flowcharts and block diagrams of methods and systems. The flowchart and block diagrams illustrate the architecture, functionality, and operation of possible implementations of systems, methods, and computer programs of the present invention. It should be understood that each block of the flowcharts and block diagrams can be implemented by computer readable program instructions in software, firmware, or dedicated analog or digital circuits. These computer readable program instructions may be implemented on the processor of a general purpose computer, a special purpose computer, or other programmable data processing apparatus to produce a machine that implements a part or all of any of the blocks in the flowcharts and block diagrams. Each block in the flowchart or block diagrams may represent a module, segment, or portion of instructions, which comprises one or more executable instructions for implementing the specified logical functions. It should also be noted that each block of the block diagrams and flowchart illustrations, or combinations of blocks in the block diagrams and flowcharts, can be implemented by special purpose hardware-based systems that perform the specified functions or acts or carry out combinations of special purpose hardware and computer instructions.

What is claimed is:

1. A system for providing control strategy for a heating, ventilation, and air condition (HVAC) system of a building, comprising:
    a controller having an input for receiving a first signal comprising data representing ambient weather information, a second signal comprising data representing an occupancy level in a location, a third signal comprising data representing a temperature of the location, a fourth signal comprising data representing an amount of outdoor air intake into the location, and fifth signal comprising data representing a quality of ambient air in the location and an output for sending a plurality of control signals governing operation of a plurality of HVAC system components that may be connected to the controller;
    a database associated with the controller and configured to record the data representing ambient weather information, the data representing the occupancy level, the data representing the temperature, and the data representing the amount of outdoor air intake over time;
    a processor associated with the controller and programmed to generate a prediction of occupancy level over a predetermined upcoming period of time based on the recorded data representing the occupancy level, to generate an estimation of carbon dioxide levels in the location based on the data representing occupancy level over time and the data representing the amount of outdoor air intake over time, and to generate a forecast of ambient air quality based on the recorded data representing ambient weather information over time and the recorded data representing the quality of ambient air in the location over time;
    wherein the processor is programmed to dynamically estimate an amount of risk of infection in the location based on the prediction of occupancy level and the forecast of ambient air quality;
    wherein the processor is programmed to determine an amount of energy required to operate the HVAC system components connected to the controller;
    wherein the processor is programmed to determine how to operate the plurality of HVAC system components to minimize the amount of energy required to operate the HVAC system components while minimizing the amount of risk of infection in the location; and
    wherein the processor is programmed to cause the controller to send the plurality of control signals governing operation of the plurality of HVAC system components based on the determination of how to operate the plurality of HVAC system components to minimize the amount of energy required to operate the HVAC system components while minimizing the amount of risk of infection in the location.

2. The system of claim 1, wherein the plurality of control signals includes an air handling unit control signal.

3. The system of claim 2, wherein the air handling unit control signal will cause a change in outside air intake.

4. The system of claim 3, wherein the air handling unit control signal will cause a change in supply air flow rate.

5. The system of claim 4, wherein the air handling unit control signal will cause a change in supply air temperature.

6. The system of claim 1, wherein the plurality of control signals includes an air filtration unit signal.

7. The system of claim 1, wherein the processor is located remotely from the controller and can communicate with the controller over the internet.

8. The system of claim 7, wherein the database is located remotely from the controller.

9. The system of claim 1, wherein the processor is programmed to determine how to operate the plurality of HVAC system components to minimize the amount of energy required to operate the HVAC system components while minimizing the amount of risk of infection in the location by implementing a multi-objective model predictive control algorithm.

10. The system of claim 9, wherein the multi-objective model predictive control algorithm considers a dynamic indoor air quality model and a coil load of any air handling unit connected to controller.

11. A method of operating a plurality of HVAC system components to minimize the amount of energy required to operate the HVAC system components while maximizing indoor air quality, comprising the steps of:
    receiving a first signal comprising data representing ambient weather information, a second signal comprising data representing an occupancy level in a location, a third signal comprising data representing a temperature of the location, a fourth signal comprising data representing an amount of outdoor air intake into the location, and fifth signal comprising data representing a quality of ambient air in the location;
    recording the data representing ambient weather information, the data representing the occupancy level, the data representing the temperature, and the data representing the amount of outdoor air intake over time;
    using a processor to generate a prediction of occupancy level over a predetermined upcoming period of time based on the recorded data representing the occupancy level, to generate an estimation of carbon dioxide levels in the location based on the data representing occupancy level over time and the data representing the amount of outdoor air intake over time, and to generate a forecast of ambient air quality based on the recorded data representing ambient weather information over time and the recorded data representing the quality of ambient air in the location over time;
    using the processor to dynamically estimate an amount of risk of infection in the location based on the prediction of occupancy level and the forecast of ambient air quality;
    using the processor to determine an amount of energy required to operate the HVAC system components connected to the controller;
    using the processor to determine how to operate the plurality of HVAC system components to minimize the amount of energy required to operate the HVAC system components while minimizing the amount of risk of infection in the location; and
    causing a controller having an output for sending a plurality of control signals governing the operation of a plurality of HVAC system components that may be connected to the controller to send the plurality of control signals governing the operation of the plurality of HVAC system components based on the determination of how to operate the plurality of HVAC system components to minimize the amount of energy required to operate the HVAC system components while minimizing the amount of risk of infection in the location.

12. The method of claim 11, wherein the plurality of control signals includes an air handling unit control signal.

13. The method of claim 12, wherein the air handling unit control signal will cause a change in outside air intake.

14. The method of claim 13, wherein the air handling unit control signal will cause a change supply air flow rate.

15. The method of claim 14, wherein the air handling unit control signal will cause a change in supply air temperature.

16. The method of claim 11, wherein the plurality of control signals includes an air filtration unit signal.

17. The method of claim 11, wherein the processor is located remotely from the controller and can communicate with the controller over the internet.

18. The method of claim 17, wherein the step of recording the data is accomplished by a database located remotely from the controller.

19. The method of claim 11, wherein the processor is programmed to determine how to operate the plurality of HVAC system components to minimize the amount of energy required to operate the HVAC system components while minimizing the amount of risk of infection in the location by implementing a multi-objective model predictive control algorithm.

20. The method of claim 19, wherein the multi-objective model predictive control algorithm considers a dynamic indoor air quality model and a coil load of any air handling unit connected to controller.

* * * * *